United States Patent
Wilson et al.

(10) Patent No.: US 9,443,419 B2
(45) Date of Patent: Sep. 13, 2016

(54) MONITORING BREATHING VIA SIGNAL STRENGTH IN WIRELESS NETWORKS

(75) Inventors: Anthony Joey Wilson, Holladay, UT (US); Neal K. Patwari, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 304 days.

(21) Appl. No.: 14/238,791

(22) PCT Filed: Aug. 16, 2012

(86) PCT No.: PCT/US2012/051171
§ 371 (c)(1),
(2), (4) Date: Jun. 30, 2014

(87) PCT Pub. No.: WO2013/025922
PCT Pub. Date: Feb. 21, 2013

(65) Prior Publication Data
US 2014/0313913 A1    Oct. 23, 2014

Related U.S. Application Data

(60) Provisional application No. 61/524,172, filed on Aug. 16, 2011.

(51) Int. Cl.
| G08C 17/02 | (2006.01) |
| A61B 5/00 | (2006.01) |
| A61B 5/08 | (2006.01) |
| H04W 4/00 | (2009.01) |
| H04W 84/18 | (2009.01) |

(52) U.S. Cl.
CPC .............. *G08C 17/02* (2013.01); *A61B 5/0816* (2013.01); *A61B 5/6889* (2013.01); *A61B 5/6891* (2013.01); *H04W 4/006* (2013.01); *H04W 84/18* (2013.01)

(58) Field of Classification Search
None
See application file for complete search history.

(56) References Cited

U.S. PATENT DOCUMENTS

| 3,911,899 A | * | 10/1975 | Hattes | A61B 5/113 128/205.23 |
| 6,011,477 A | * | 1/2000 | Teodorescu | A61B 5/113 340/573.1 |

(Continued)

FOREIGN PATENT DOCUMENTS

WO    2013025922    2/2013

OTHER PUBLICATIONS

Kao et al., Wireless Sudden Infant Death Syndrome Detection System. May 3, 2005 [retrieved on Oct. 11, 2012]. Retrieved from the Internet: <URL:http://courses.engr.illinois.edu/ece445/projects/spring 2005/project39_final_paper.doc>.

(Continued)

*Primary Examiner* — Dung B Huynh
(74) *Attorney, Agent, or Firm* — Workman Nydegger

(57) ABSTRACT

Systems and methods are disclosed for the use of sensor links in a network to estimate the breathing rate of a breathing subject within a structure, estimate the location of the subject within the structure, and detect if the subject is breathing. The structure may be a bed, a building, or a room in the building. The received signal strength of the sensor links is obtained and is then used in various breathing models to determine the breathing rate estimation, the location estimation, and the breathing detection.

53 Claims, 12 Drawing Sheets

(56) References Cited

U.S. PATENT DOCUMENTS

| | | | | |
|---|---|---|---|---|
| 6,266,551 | B1* | 7/2001 | Osadchy | A61B 1/00059 600/424 |
| 2004/0210155 | A1* | 10/2004 | Takemura | A61B 5/00 600/534 |
| 2006/0270941 | A1* | 11/2006 | Xie | A61B 5/4818 600/529 |
| 2008/0039736 | A1* | 2/2008 | Nemoto | A61B 5/11 600/544 |
| 2008/0074307 | A1* | 3/2008 | Boric-Lubecke | A61B 5/0205 342/28 |
| 2008/0139955 | A1 | 6/2008 | Hansmann et al. | |
| 2010/0026479 | A1 | 2/2010 | Tran | |
| 2011/0160584 | A1* | 6/2011 | Paul | A61B 8/0883 600/439 |
| 2012/0184862 | A1* | 7/2012 | Foo | A61B 5/1102 600/508 |

OTHER PUBLICATIONS

International Search Report and Written Opinion. PCT/US2012/051171. United States International Search Authority, Completion of Search Report Oct. 12, 2012, Mailing of Search Report Oct. 25, 2012.

* cited by examiner

MONITORING BREATHING VIA SIGNAL STRENGTH IN WIRELESS NETWORKS

CROSS-REFERENCE TO RELATED APPLICATIONS

This application claims the benefit of and priority to PCT Application No. PCT/US2012/051171, filed Aug. 16, 2012, entitled "Monitoring Breathing Via Signal Strength in Wireless Networks", which claims the benefit of and priority to U.S. Provisional Application No. 61/524,172, filed Aug. 16, 2011, entitled "Monitoring Breathing Via Signal Strength in Wireless Networks", each of which is incorporated herein by reference in its entirety.

STATEMENT REGARDING GOVERNMENT RESEARCH AND DEVELOPMENT

This invention was made with Government support under 1035565 and ECCS0748206 awarded by the National Science Foundation. The Government has certain rights in this invention.

BACKGROUND

Breathing monitoring has many useful applications in today's world. For example, post-surgical patients can die from respiratory depression and airway obstruction, which are unfortunately common after surgery due the difficulty of correctly dosing sedatives and pain medications administered to a patient. Reliable respiration monitoring is critical to detection of these conditions Breathing monitoring also has application in diagnosis and treatment for obstructive sleep apnea, in which a person experiences periods of low breathing rate or long pauses in breathing while sleeping. Furthermore, breathing monitoring may have application in detecting sudden infant death syndrome (SIDS), which is one of the largest causes of death in infants. Parents with a child with one or more risk factors for SIDS may wish to use a baby breathing monitor to alert them in case their child's breathing becomes depressed or stops. Thus, it may be desirable to monitor the breathing of a patient.

SUMMARY

An embodiment disclosed herein is related to methods and systems for breathing rate estimation. A plurality of sensors in a network are arranged around a subject within a structure. A received signal strength (RSS) between the plurality of sensors is measured, the measured RSS being at least partially indicative of breathing of the subject. A breathing rate estimation model based on information related to the measured signal strengths is determined. A breathing rate of the subject is estimated using the breathing rate estimation model.

An embodiment disclosed herein is related to methods and systems for breathing detection. A plurality of sensors in a network are arranged around a subject within a structure. A received signal strength between the plurality of sensors is measured, the measured received signal strength being at least partially indicative of breathing of the subject. A network-wide breathing statistic over all links of the plurality of sensors is determined based on information related to the measured signal strengths. Finally, a determination of whether the subject is breathing or nor is made using the network-wide breathing statistic.

An embodiment disclosed herein is related to methods and systems for estimating the location of a breathing subject within a structure. A breathing rate estimate of a subject within a structure is obtained, the breathing rate estimate based at least in part on the measured signal strength obtained from a plurality of sensors within the structure. The breathing rate estimate is imputed into a breathing localization model, the breathing localization model configured to estimate one or more coordinates within the structure where the subject is located. An estimation of the location of the subject within the structure based on the coordinates obtained from the breathing localization model The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1:
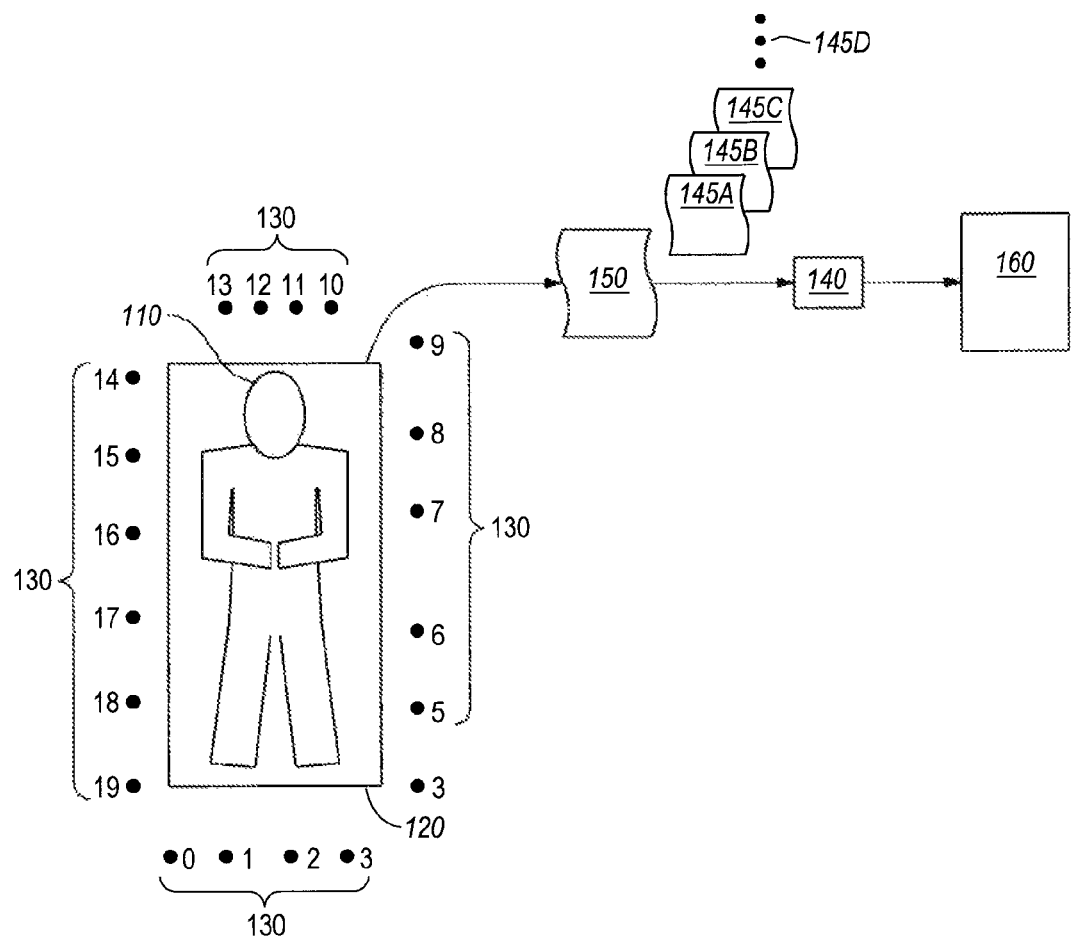
FIG. 1 illustrates a system for implementing the embodiments disclosed herein.

In the following detailed description, reference is made to the accompanying drawings, which form a part hereof. In the drawings, similar symbols typically identify similar components, unless context dictates otherwise. The embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. It will also be understood that any reference to a first, second, etc. element in the claims or in the detailed description, is not meant to imply numerical sequence, but is meant to distinguish one element from another unless explicitly noted as implying numerical sequence.

The embodiments disclosed herein are directed towards the use of sensor links in a wireless or other type of network to estimate the breathing rate of a breathing subject within a structure, estimate the location of the subject within the structure, and detect if the subject is breathing. The structure may be a bed, a building, or a room in the building. The received signal strength of the sensor links is obtained and is then used in various breathing models to determine the breathing rate estimation, the location estimation, and the breathing detection.

Attention is given to FIG. 1, which illustrates a system 100 that may be used to implement the embodiments disclosed herein. As illustrated, the system 100 includes a living subject 110 whose breathing may be detected and estimated, for example a human. It will be appreciated that the subject 110 may represent more than one subject being, in some embodiments. It will also be appreciated that although the embodiments disclosed herein will generally be applied to the subject 110, the embodiments may also be applied to other breathing organisms such as animals. Accordingly, although the discussion below will refer generally to humans such as the subject 110, other breathing organisms such as animals may also have their breathing detected and estimated by the embodiments disclosed herein.

The system 100 further includes a structure 120 that supports and/or holds the subject 110. In one embodiment, the structure 120 may be a hospital bed or other bed that the subject 110 may lay on. One example bed may be a Hill-Rom P1900 bed that automatically changes pressure in different parts of the bed every 3-4 minutes. In another example, the bed may include an operation table or any other structure that can support and/or hold the subject 110. Accordingly, the embodiments disclosed herein for breathing rate estimation and breathing detection may be implemented in a medical environment to estimate and detect breathing of patients in hospital, hospice, doctor's office, or other medical facility.

In addition, if the structure 120 is a crib or other bed that a baby or young child sleeps in, then the embodiments disclosed herein for breathing rate estimation and breathing detection may be implemented in the home by the parents and/or guardians to monitor a baby's breathing to prevent SIDS or similar childhood problems. Further, if the structure 120 is an adult bed, then the embodiments disclosed herein for breathing rate estimation, breathing localization, and breathing detection may be implemented in the home by the adult to monitor against sleep apnea and other breathing related ailments.

The system 100 also includes a network of sensors 130 numbered 0-19 that are located and/or oriented with respect to the structure 120, which in the embodiment of FIG. 1 is a bed. In most embodiments, no sensor 130 is attached to the subject 110. Since the sensors 130 are not attached to the subject 110, any breathing of the subject 110 will not result in movement of the sensors 130. However, in some embodiments, the sensors 130 may be attached to the subject 110 as circumstances warrant.

It will be appreciated that although FIG. 1 illustrates twenty sensors 130, a larger or smaller number of sensors 130 may be utilized as circumstances warrant. Although the group of sensors 10-13 and the group of sensors 0-3 are shown as being in parallel (as are the group of sensors 14-19 and the group of sensors 4-9, with respect to each other), other locations and/or orientations of the sensors are contemplated. For example, a more elliptical array of sensors may be used. Furthermore, although the sensors 130 are shown as lying in the same vertical plane, other vertical relationships are also contemplated. In addition, more sensors 130 may be provided than are actually used. For example, a larger array of sensors 130 that may or may not be aligned in three-dimensional space may be used to accommodate, for example, larger and/or smaller subjects (i.e. one or more additional sets of sensors 130 located above the array of sensors 130 shown in FIG. 1, a three dimensional ellipse of sensors 130, or other configurations).

Although the specific location of the sensors 130 is provided and may be necessary for some of the above embodiments, in other embodiments, the sensors 130 may be configured to form their own network (such as network 150 described below) and detect a breathing subject 110, for example in a search and rescue application. In such an application, the sensor 130 might be deployed into the rubble of a collapsed building. In one embodiment, the sensors 130 may be thrown or otherwise placed into the rubble by the rescuers. Alternatively, robotic means may be employed to actively move the sensors 130 into gaps in the collapsed building. Once the sensors 130 are stationary in the collapsed building, they may form a network by communicating with other sensors 130. In an alternative embodiment, the sensors 130 may be part of an existing network in the building prior to the collapse, for example a WiFi network or other wireless network in the building. In this case, the sensors 130 may be configured to form a network after the building collapses.

Figure 9:
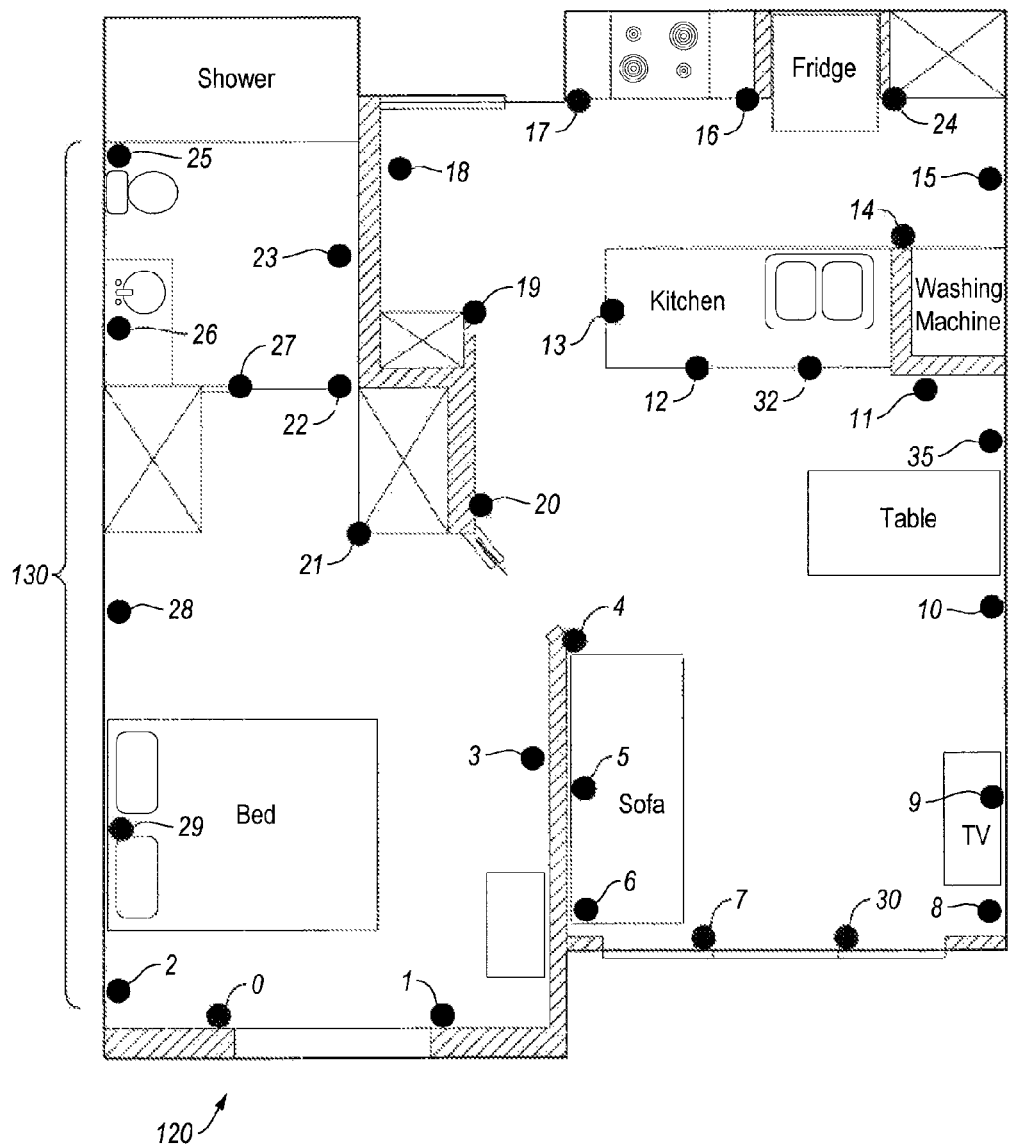
FIG. 9 illustrates a structure implemented as an apartment in accordance with an embodiment disclosed herein.

In some embodiments, the structure 120 may be a building or house, an apartment, or a room inside of the building, house or apartment where the subject 110 may be located. It will be appreciated that the structure 120 may be anything that can support and/or hold the subject 110 or where the subject 110 may be located. Additionally, the structure 120 can have a network of sensors attached to it as will be explained. For example FIG. 9 illustrates an embodiment where the structure 120 is an apartment. In this embodiment, a network of sensors 130 numbered 0-32 are placed or located at various locations in the apartment 120. Typically, the sensors 130 may be implemented inside of the walls of the apartment 120 when the apartment is constructed or the sensors 130 may be attached externally to the walls. It will be appreciated that the sensors 130 may be attached to the apartment 120 in other reasonable ways and that more or less than 33 sensors 130 may be implemented as circumstances warrant.

Advantageously, implementing the embodiments disclosed herein for breathing rate estimation, breathing detection, and breathing localization when the structure 120 is a building or the like may allow for detection of subjects 110 inside of a burning building or a collapsed building and may aid rescue workers in determining where to search and provide aid. In addition, police officers may use the embodiments disclosed herein to determine if a person is inside of a building or a room, thus preventing any surprise attacks as the police officers enter the building or the room. Further, placing the sensors 130 in the walls of the structure 130 may be help to provide monitoring of an aged person or a person with a breathing aliment that needs constant monitoring without the need to use conventional monitoring systems.

In some embodiments, regardless of the type of structure 120, the sensors 130 may be a wireless device that operates in any desirable frequency band. In other embodiments, the sensors 130 may be wired. The sensors 130 may include both a transmitter able to transmit a signal or data packet. In addition, the sensors 130 may also include a receiver that receives information related to the received signal strength (RSS) of a transmitted signal as will be described in more detail to follow. In other embodiments, the sensors 130 may comprise separate transmitter sensors and separate receiver sensors. It will be appreciated that a link is generated between a sensor 130 (for example, sensor number 10) that transmits a signal to another sensor 130 (for example, sensor number 19) that receives the signal. Thus, in the embodiment of FIG. 1 where twenty sensors 130 are implemented, there may be 380 links generated between the twenty sensors 130. In the embodiment of FIG. 9, there may be 1056 links.

In one embodiment, the sensors 130 may comprise a network of twenty MEMSIC TelosB wireless sensors operating the IEEE 802.15.4 protocol on channel 26 having a center frequency of 2480 MHz. These sensors 130 may run TinyOS and SPIN, which is a token passing protocol in which each sensor transmits in sequence, to avoid collisions. When not transmitting, these sensors 130 are in receive mode, and record RSS information 145 and node id for any data packet from another of the sensors 130. Each transmitted data packet includes the most recent RSS information 145 recorded for each other sensor 130. These sensors may be implemented with a mesh topology, although other network topologies may also be used as circumstances warrant. For example, other network topologies may include a "star" shape, where one transmitter broadcasts to multiple receivers. Furthermore, it will be appreciated that each sensor 130 in the sensing network need not be both a transmitter and receiver, nor does there need to be the same amount of transmitters and receivers for the system to function.

In an alternative embodiment, the sensors 130 may comprise sensors that can operate on multiple frequency channels. For example, the sensors 130 may be multiple frequency channel TI CC2531 wireless sensors that are IEEE 802.15.4 compliant operating in the 2.4 GHz ISM band. A TDMA protocol may be used in which each sensor 130 transmits in sequence on a first frequency channel and after each sensor has transmitted, the sensors 103 synchronously switch to the next frequency channel. In one embodiment, four frequency channels with IEEE 802.15.4 channels 15, 20, 25, and 26 may be utilized and each sensor 130 may be measured for 428 ms for each channel. It will be appreciated that using a multiple frequency channel sensor 130 provides for a larger number of samples over a single channel sensor. For instance, in the embodiment using four frequency channels, four times as many samples would be measured over a single channel sensor.

In one embodiment, the sensors 130 are communicatively coupled to a base station sensor 140 via a network 150. The network 150 may be any network that is compatible with the sensors 130 and may include, by way of example, satellite networks, 802 networks, personal computer networks (e.g., LAN, WAN), wireless networks (e.g., Bluetooth, WiFi), cellular networks, telephony networks (e.g., landline or PSTN), data networks, the Internet, or the like or any combination thereof.

The base station sensor 140 may receive data packets including the most recent RSS information 145A, 145B, 145C, and any number of additional RSS information as illustrated by the ellipses 145D (hereinafter referred to as RSS information 145) transmitted by the sensors 130. It will be appreciated that the number of RSS information 145 will be determined by the number of sensors 130 and the links created between the sensors 130. In other embodiments, the base station sensor may overhear the transmitted RSS information 145. In one embodiment, the base station sensor 140 may be placed approximately three meters from the structure 120 and the sensors 130. The base station sensor 140 may then provide the RSS information 145 to the computing system 160.

In one embodiment, a data packet may be transmitted by one of the sensors 130 approximately once every 12 ms, and thus an individual sensor 130 may transmit once every 240 micro second. Thus, in this embodiment, each link has its RSS measured at a sampling rate of 4.16 Hz.

As discussed above, the base station sensor 140 may then provide the RSS information 145 to the computing system 160. In some embodiments, the base station sensor 140 may be part of the computing system 160. As will be described, the computing system 160 may use the RSS information 145, which includes the RSS of the various sensors 130, to estimate the breathing rate and/or to detect breathing of the subject 110.

In other embodiments, the system 100 may not include the base station sensor 140. In such embodiments, the sensors 130 may transmit the RSS information 145 directly to the computing system 160. In addition, in some embodiments, the computing system 160 may be a distributed system where processing is preformed in a distributed manner on more than one device. In one embodiment, the sensors 130 may include processing resources and may constitute the distributed computing system.

Figure 2:
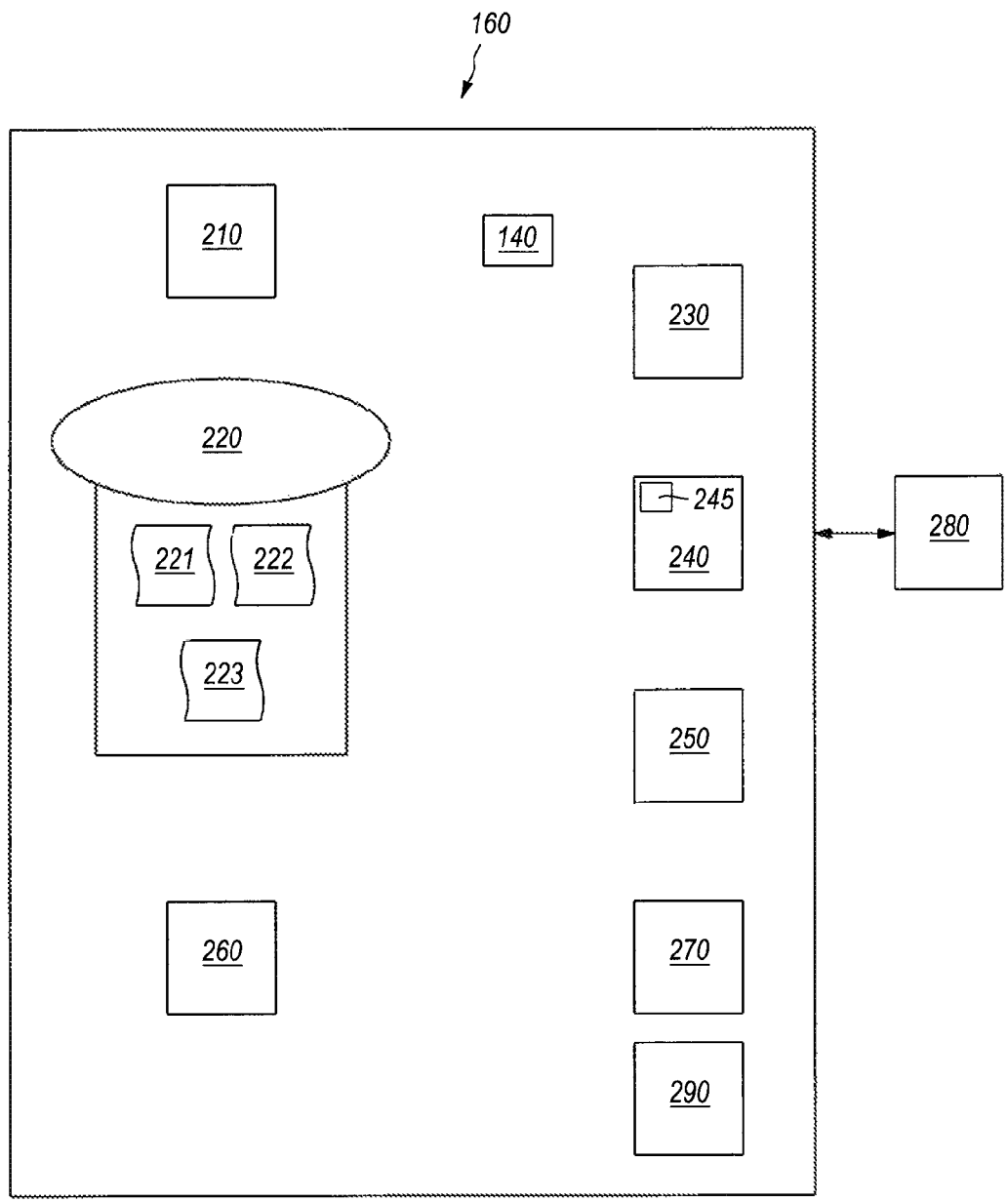
FIG. 2 illustrates a computing system for use in the system of FIG. 1.

Attention is now given to FIG. 2, which shows an example of a computing system 160. As shown, the computing system 160 includes various operational modules and databases that will be explained in more detail. Although not shown as being coupled, so as to not distract from the embodiments disclosed herein, it will be understood that the various operational modules and databases of the computing system 160 may be coupled to each other by any reasonable means such as a computer bus, other wiring, or wireless connection as circumstances warrant.

As shown, the computing system 160 includes a processor 210. The processor 210 may be any reasonable processor and in operation allows the computing system 160 to perform various operations. In some embodiments, the processor 210 may be accessed by the various operational modules of the computing system 160 to provide the modules processing resources. In other embodiments, the operational modules may have access to an alternative processor.

The computing system 160 also includes a database 220. The database 220 may be any type of reasonable non-volatile or volatile memory and may be used to store information. In one embodiment, the database 220 may store a minimum expected breathing frequency 221 and a maximum expected breathing frequency 222. Adult humans have a breathing rate of about 14 breaths per minute and babies have a breathing rate of about 37 breaths per minute. Thus, in one embodiment, the minimum breathing frequency 221 may be equal to 10 breaths per minute or 0.167 Hz. The maximum breathing frequency 222 may be equal to 40 breaths per minute or 0.667 Hz. This range covers both the typical adult and baby ranges. The database 220 may also store a threshold 223 that is used in breathing detection and/or breathing estimation as will be described in more detail to follow.

The computing system 160 includes a breathing rate estimation module 230 and/or a breathing detection module 240. As will be explained in more detail to follow, the breathing rate estimation module 230 may use the RSS information 145 to estimate a breathing rate for the subject 110. Likewise, the detection module 210 may use the RSS information 145 and the threshold 223 to detect whether or not the subject 110 is breathing.

The computing system 160 may further include a phase estimation module 250. As will be described in more detail to follow, the phase estimation module 250 may use the RSS information 145 to estimate the number of subjects 110 are within the structure 120. In other embodiments, other modules, such as a spectral estimation module (not shown) may be used instead of or in conjunction with the phase estimation module 250. The other modules may use the RSS information 145 to estimate the number of subjects 110 within the structure 120.

The computing system 160 may also include a filter module 260. In some embodiments, the filter module 160 may be used to filter out low frequency or DC components of the RSS information 145. In one embodiment, the filter module 260 may be implemented as a $7^{th}$ order high-pass Chebychev filter with a maximum passband ripple of 0.1 dB and a passband frequency of 0.167 Hz. The filter module 260 may improve the performance of the breathing rate estimation module 230 and/or the breathing detection module 240.

In some embodiments, the computing system 160 may include a breathing pattern generator 270. In operation, the breathing pattern generator may graphically show an amplitude of the RSS information 145 to thereby show a continuous breathing pattern for the subject 110.

A user interface 280 may also be part of or operationally coupled to the computing system 160. The user interface 280 may show the breathing pattern generated by the breathing pattern generator 270. In addition, the user interface 280 may allow a user to interact with the various modules previously described.

The computing system 160 may further include a localization module 290. As will be explained in more detail to follow, the breathing localization module 290 may use the RSS information 145 to estimate a location of the subject 110 while in a building.

Signal Model

As previously described, the computing system 160 receives the RSS information 145 from the various sensors 130 via the base station sensor 140 or directly from the sensors. In one embodiment, the RSS information 145 for any given link in the absence of a breathing subject 110 may be denoted as, $$yl(i)=\bar{y}l+\epsilon l(i) \quad (1)$$

where $\bar{y}l$ is the mean RSS for a link l and $\epsilon l(i)$ is additive noise. The noise of the link may be zero-mean Gaussian noise.

In the presence of a breathing subject 110, the RSS information 145 may also include a sinusoidal term and may be denoted as, $$yl(i)=\bar{y}l+A_l \cos(2\pi f T_s i+\phi l)+\epsilon l(i) \quad (2)$$

where $A_l$, $\phi l$, and f are the amplitude, phase, and frequency, respectively, of the periodic component of the RSS signal on link l and $T_s$ is the sampling period. It may be assumed that the periodic component due to breathing would have the same frequency on all links l and that the sampling period is made to be identical on all links, thus a subscript l for frequency f need not be used. In most embodiments, phase and amplitude are expected to differ between links l.

In some embodiments, an observation period T may be denoted as $T=NT_s$, where N is the total number of samples. The observation period T is related to the latency of breathing monitoring and may be used to specify various time periods that breath rate estimation and/or breath detection may occur.

As will be appreciated, when estimating the power spectral density of noisy, finite-duration yl signals, the mean values $\bar{y}l$ (the DC component) can "hide" the power of lower-amplitude sinusoidal components. However, the DC component does not hold information about the presence or absence of breathing since the frequency of the DC components will be below the minimum breathing frequency 221 discussed previously. Accordingly, in some embodiments the filter module 260 may be used to implement a high pass filter that filters out the DC components from the RSS information 145. Thus the RSS information 145 provided to the breathing rate estimation module 230 and/or the breathing detection module 240 in those embodiments that implement filter module 260 will typically have the DC component filtered out.

Breathing Estimation Model

In one embodiment, the breathing rate breathing rate estimation module 230 may estimate the breathing rate of the subject 110 by determining a breathing rate estimation model that maximizes a function of the received signal strengths of various sensor pairs of the sensors 130. In one embodiment, determining the breathing rate estimation model may include determining the maximum likelihood estimate (MLE) of breathing parameters, including frequency, link amplitudes, and link phases.

Maximum likelihood estimation of the breathing parameters is an extension of the standard sinusoid parameter estimation problem in which there is a single signal composed of one sinusoid of unknown phase, amplitude, and frequency in additive white Gaussian noise. In the present embodiment, additionally there are L different link signals, each with its own amplitude and phase, where L is the number of links between the various sensors 130. In addition, as previously discussed, the frequency range is limited to the minimum breathing frequency 221 and the maximum breathing frequency 222.

In the present embodiment, the likelihood function is maximized when the following function J is minimized:

$$J(\theta)=\Sigma_{l=1}^{L}\Sigma_{n=i-N+1}^{i}[yl(n)-A_l\cos(2\pi fTn+\phi l)]^2 \quad (3)$$

where L is the number of links between the various sensors 130 and N is the total number of samples taken by each sensor 130 to produce the RSS information 145.

The equation (3) may be modified as follows to determine the MLE of frequency of $\hat{f}$.

$$\hat{f} = \underset{f_{min} \le f \le f_{max}}{\text{argmax}} \sum_{l=1}^{L}\left|\sum_{n=i-N+1}^{i} yl(n)e^{-j2\pi fT_n}\right|^2 \quad (4)$$

where $f_{min}$ and $f_{max}$ are the minimum and maximum breathing rates the system is set to allow, i is the current time, N is the number samples, and yl(n) is the change in the RSS information 145. The maximum likelihood link amplitude estimates $\{\hat{A}_l\}$ and phase estimates $\{\hat{\phi}l\}$ are given by:

$$\hat{A}_l = \frac{2}{N} \left| \sum_{n=i-N+1}^{i} yl(n) e^{-j2\pi \hat{f} T n} \right| \quad (5)$$

$$\hat{\phi}l = \arctan \frac{-\sum_{n=i-N+1}^{i} yl(n)\sin 2\pi \hat{f} T n}{\sum_{n=i-N+1}^{i} yl(n)\cos 2\pi \hat{f} T n}$$

Accordingly, as mentioned above, the breathing rate estimation module 230 may use the RSS information 145 and the equation (4) with L set to the total number of links to determine the breathing rate for the subject 110. For the embodiment disclosed in FIG. 1, L is 380 links. Thus, the total power spectral density of all the links is used to determine the breathing rate of the subject 110.

As mentioned previously, in some embodiments the filter module 260 is used to remove the mean RSS. In other embodiment, however, the mean RSS may be removed by the breathing rate estimation module 230 or some other module of the computing system. For example, in one embodiment the change in the RSS compared to the mean is defined as:

$$yl[n] = r_l[n] - \bar{r}_l \quad (6)$$

where $\bar{r}_l$ is the mean RSS on link l. In one embodiment $\bar{r}_l$ is defined as:

$$\bar{r}_l = \frac{1}{N} \sum_{n=i-N+1}^{i} r_l[n] \quad (7)$$

Accordingly, in this embodiment, the mean RSS value is removed in equation (6). After the removal, the new RSS signal yl[n] is then used in equation (4) to perform breathing rate estimation.

As will be appreciated, any motion of the subject 110 that is not related to breathing such as a twitch, a cough, the subject moving a limb, moving or rolling over in the bed or the building 120 may cause motion interference in the breathing estimation. However, it has been observed that motion interference causes a different type of RSS change than does breathing. For example, breathing may cause slow, periodic RSS changes; motion interference may cause sudden changes.

Accordingly, in some embodiments the breathing rate estimation module 230 or some other module of the computing system 160 may detect each time index, referred to herein as a breakpoint or breakpoint index, during which a sudden RSS change occurs that may be related to motion interference. At each breakpoint, the system is allowed to forget a previous RSS average and calculate a new average. The breakpoint is used to help remove the mean RSS value.

In one embodiment, a group t-score is first computed:

$$\tau_l[n] = \frac{\grave{r}_l[n] - \acute{r}_l[n]}{\max\left\{\epsilon, \sqrt{\grave{\sigma}_l^2[n] + \acute{\sigma}_l^2[n]/Q}\right\}} \quad (8)$$

for each link l and time t, where $\grave{r}_l[n]$ is and $\acute{r}_l[n]$ are the average of Q samples of $r_l[m]$ before and after time n, respectively, $\grave{\sigma}_l^2[n]$ and $\acute{\sigma}_l^2[n]$ are the sample variances of $r_l[m]$ before and after time n, respectively, and $\epsilon > 0$ is used to prevent division by zero. In one embodiment, $\epsilon = 0$.

Next, at each time n a root-mean squared (RMS) average of $\tau_l[n]$ over all links l is computed:

$$\tau_{RMS}[n] = \left( \frac{1}{L} \sum_{l=1}^{L} \tau_l^2[n] \right)^{\frac{1}{2}} \quad (9)$$

Time n is a breakpoint index if $\tau_{RMS}[n] \geq \gamma$, where $\gamma$ is a predetermined threshold such as threshold 223. For any time window, the starting time index and the ending time index may be considered breakpoints. At the current time i, with a window length N, the starting and ending indices are i−N+1 and i.

Breakpoints may then be used to remove the mean RSS as follows:

$$yl[n] = r_l[n] - \tilde{r}_l[n] \quad (10)$$

where $\tilde{r}_l[n]$ is the average of $r_l[m]$ for all m such that $b_p \leq m < b_f$, where $b_p$ is the latest breakpoint before or at time index n and $b_f$ id the earliest breakpoint after time index n. Thus, the mean model $\tilde{r}_l[n]$ is a piecewise constant with transition times at each breakpoint.

Accordingly, in this embodiment, the mean RSS value is removed in equation (10). After the removal, the new RSS signal yl[n] is then used in equation (4) to perform breathing rate estimation.

Figure 10:
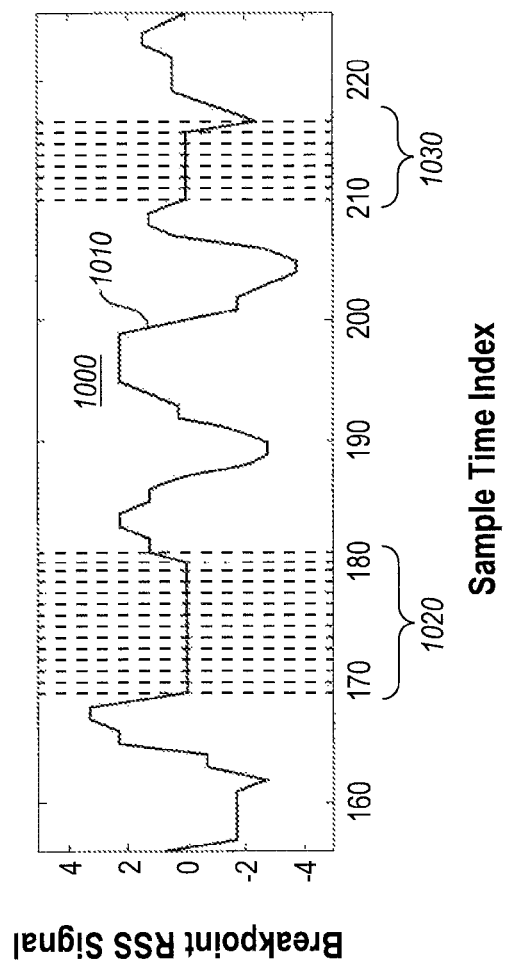
FIG. 10 illustrates a plot 1 of an RSS signal using the breakpoint method to remove the mean in accordance with an embodiment disclosed herein.

FIG. 10 shows a plot 1000 of an RSS signal using the breakpoint method previously described to remove the mean. In this embodiment, the predetermined threshold $\gamma$ is equal to 0.8. The plot 1000 shows a plot line 1010 that shows the RSS signal. As illustrated, FIG. 10 shows that a high RMS t-score is found near time index 175 and 213, indicating a shift in the mean near these two time indices. In addition, several breakpoints are found near these two time indices. By removing the mean between the breakpoints, the RSS signal is prevented from having a drifting mean. In some ranges, such as range 1010 seen between approximately 169 and 181 and range seen between approximately 210 and 215, the mean is reduced to zero because the breakpoints are dense in these ranges.

Breathing Detection Model

In another embodiment, the breathing detection module 240 may detect if the subject 110 is breathing. In order to perform breathing detection, two different states are considered:

$H_0$:A breathing person is not present (11)

$H_1$:A breathing person is present (12)

During operation, for all L measured links, the breathing detection module 240 needs to decide between $H_0$ and $H_1$, that is whether a breathing subject 110 is present or not. The breathing detection may be based on a normalized sum of the squared amplitudes $\hat{A}_l^2$ over links, $$\hat{S} \triangleq \frac{N}{L} \sum_{l=1}^{L} \hat{A}_l^2 \underset{H_0}{\overset{H_1}{\gtrless}} \gamma_{net} \quad (13)$$

where $\gamma_{net}$ is a user defined threshold such as threshold 223 and $\hat{S}$ is a network-wide breathing statistic. Note that $\hat{S}$ is the scaled version of the maximum sum of equation (4). Multiplication of the average squared link magnitude by N helps to ensure a constant threshold as a function of N, since the average squared link magnitude is approximately inversely proportional to N under $H_0$.

Breathing Localization Model

In some embodiments, the breathing localization module 290 may be used to determine a breathing localization model that may be used to compute where the breathing at the rate estimated by the breathing estimation module 230 is occurring when the subject 110 is in a structure 120 that is a building or a room of a building. The breathing estimate for each sensor link l is used as an input to the model as follows:

$$v_l = |\Sigma_{n=i-N+1}^{i} y_l(n) e^{-j2\pi f T n}|^2 \quad (14)$$

The vector of all link values is $v = |v_1, \ldots, v_L|^T$. In the embodiment, it is desirable to estimate an image of breathing amplitude vs. space, denoted vector x, where $x_k$ represents the quantity of breathing energy coming from a pixel k. It is assumed that v is a linear combination of x via a weighting matrix W plus noise $\eta$, $$v = Wx + \eta \quad (15)$$

where W is defined as having (l,k) elements given by:

$$W_{l,k} = \begin{cases} \frac{1}{P_l}, & \frac{\|zT_l - p_k\| + \|zR_l - p_k\|}{\|zT_l - zR_l\| + \lambda_e} \leq 1 \\ 0, & o.w \end{cases} \quad (16)$$

where $zT_l$ and $zR_l$ are the coordinates of TX and RX for link l, respectively, and $p_k$ is the coordinate of the pixel k, $\lambda_e$ is the ellipse size parameter, and $P_l$ normalizes the weight so that the total weight of the each link is 1.

It is assumed that the image vector has a covariance matrix G, with (k,m) element $G_{k,m} = \sigma_x^2 e^{-\|z_k - z_m\|/\delta}$, where $\sigma_x^2$ is the variance of any element of x, and $\delta$ is the correlation distance. The regularized least squares solution for x is thus:

$$\hat{x} = \Pi v, \text{where } \Pi = (W^T W + G^{-1})^{-1} W^T \quad (17)$$

It is noted that $\Pi$ need only be computed once. The real-time computation of the image requires only one matrix multiply, of O(LP) multiplies and adds, where P is the number of pixels. From the image the coordinate of the pixel with the maximum value in $\hat{x}$ is used as the location estimate for the breathing subject 110.

Performance Analysis

In some embodiments, it may be useful to study the performance analysis of the breathing rate estimation and/or breathing detection performed by the computing system 160. In such embodiments, a performance may be measured by having the computing system 200 determine a Root Mean Square Error (RMSE) of $\hat{f}$, $$\text{RMSE} = \sqrt{\frac{1}{K} \sum_{k=1}^{K} [\hat{f}(k) - f(k)]^2} \quad (18)$$

where $\hat{f}(k)$ and $f(k)$ are the frequency estimate and the actual breathing frequency, respectively, during experimental realization k and there are K total experimental realizations.

Breathing Estimation

Operation of the breathing rate estimation module 230 will now be explained. In one experimental embodiment, a subject 110 is placed in a bed, which is an example of a structure 120. The subject 110 listens to a metronome set to a desired breathing rate, and ensures that he or she breathes at the same rate as the metronome. The subject 110 is also connected to an end-tidal $CO_2$ monitor, which involves tubes, two to feed oxygen into the person's nostrils, and another two to connect the first tubes to a gas sensor which measures $CO_2$ and displays it on a screen. The breathing rate estimation module 230 may then estimate the breathing of the subject 110 using equation (4) and the model described above. As mentioned previously, a network-wide estimate is determined by setting L in equation (4) to the total number of links, which, in the embodiment of FIG. 1, is 380.

Figure 3:
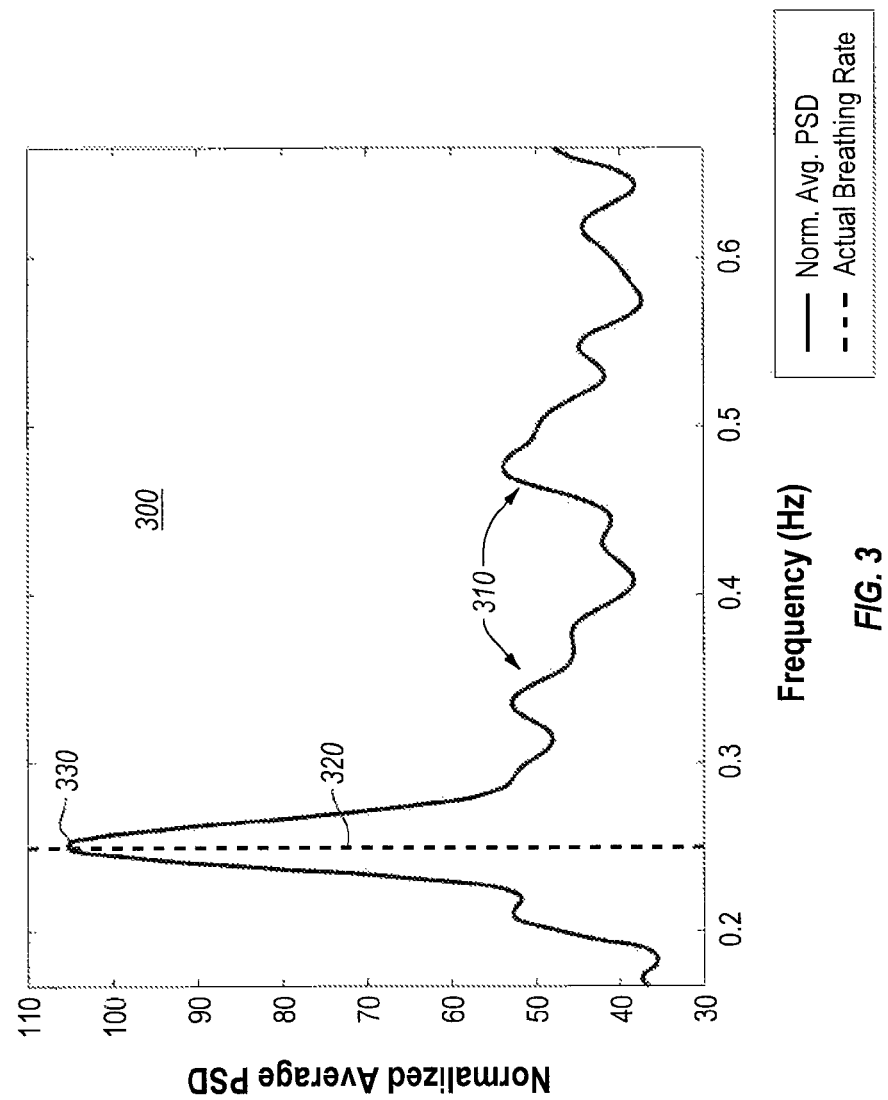
FIG. 3 illustrates 3 a plot showing the average power spectral density (PSD) versus frequency (Hz) in accordance with an embodiment disclosed herein.

FIG. 3 illustrates a plot 300 showing the average power spectral density (PSD) versus frequency (Hz) for the experimental embodiment disclosed herein. It will be noted that the total PSD is defined as the argument of equation (4). As can been seen, the plot 300 includes a PSD plot line 310 that shows the PSD at various frequencies. The plot 300 also shows a dashed line 320 that represent an actual breathing rate of the subject 110 measured with the $CO_2$ monitor when the subject 110 breathed with the metronome. This actual breathing rate is approximately 0.250 Hz (15 breaths per minute (bpm)). A peak 330 of the PSD plot line 310 is at approximately 0.253 Hz (15.18 bpm). Comparing the actual breathing rate with the peak of the PSD shows that the breathing rate estimation performed by the breathing rate estimation module 230 is very accurate and able to closely approximate an actual breathing rate.

Figure 11:
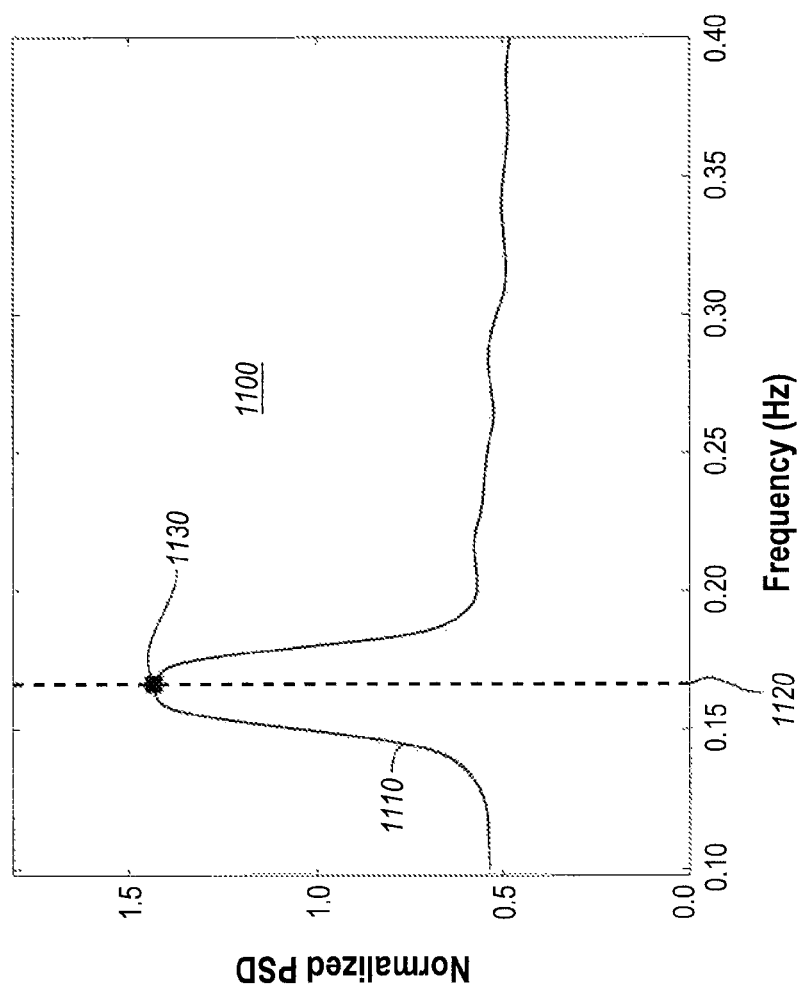
FIG. 11 illustrates a plot showing the average PSD versus frequency (Hz) using the breakpoint method in accordance with an embodiment disclosed herein.

FIG. 11 illustrates a plot 1100 showing the average PSD versus frequency (Hz) for an experimental embodiment using the breakpoint method. The plot 1100 shows a PSD plot line 1110 that shows the PSD value at various frequencies. The plot 1110 also shows a dashed line 1120 that represents an actual breathing rate of a subject 110, which in this embodiment is approximately 0.167 Hz. A peak 1130 of the PSD line 1110 is at approximately 0.166 Hz, which is very close to the actual breathing rate. Comparing the actual breathing rate with the peak of the PSD shows that the breathing rate estimation performed by the breathing rate estimation module 230 using the breakpoint method is very accurate and able to closely approximate an actual breathing rate.

As mentioned, the rate estimation performance for a variety of different periods T. The vast majority of breathing rate estimates fall within 5 bpm of the actual rate—a small fraction do not. The estimates that are more than 5 bpm from the actual rate may be considered "invalid" rate estimates. A percentage of rate estimates that are invalid may be reported by the computing system 160. The RMSE and bias of the estimates that are valid, i.e., within 5 bpm of the true rate, may also be reported.

Figure 4:
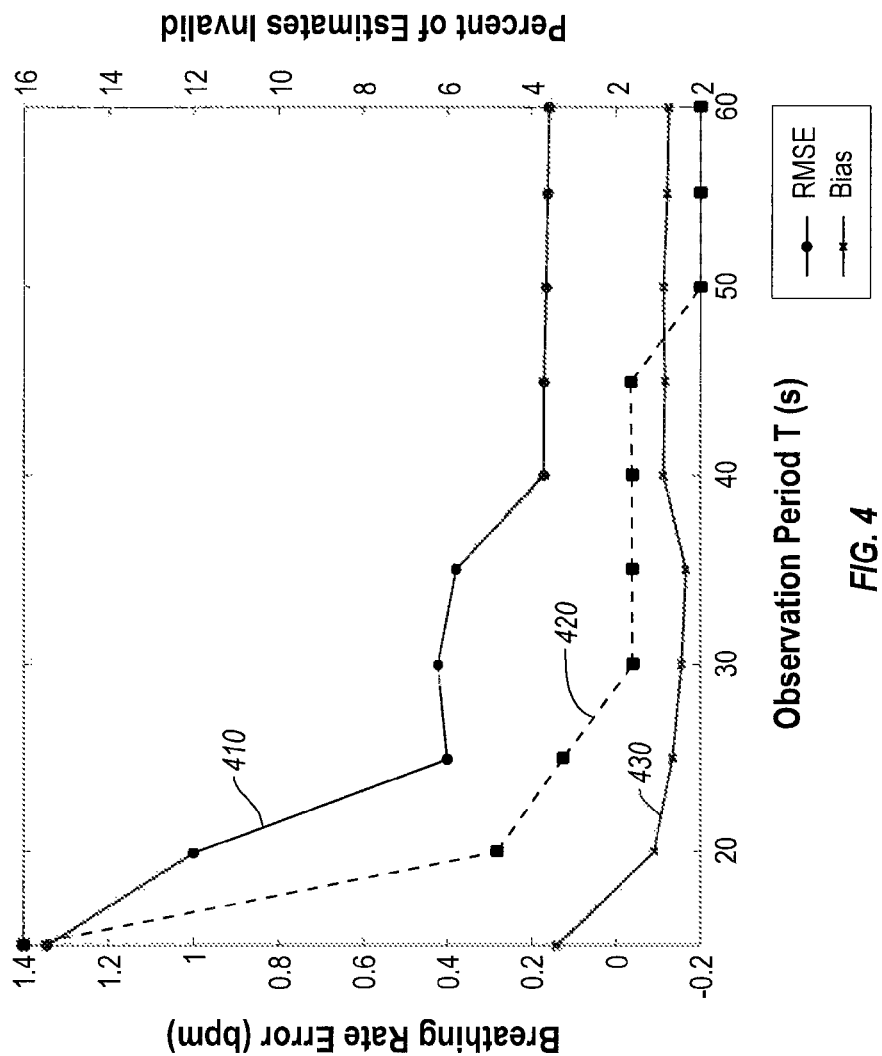
FIG. 4 illustrates RMSE values percent invalid values, and bias values versus an observation period in accordance with an embodiment disclosed herein.

FIG. 4 illustrates RMSE values 410, percent invalid values 420, and bias values 430 versus an observation period. FIG. 4 also shows that for an observation period T≥30 s, less than 2% of rate estimates can be described as invalid. The RMSE for valid estimates is lower than 0.5 for all observation periods T≥25 s. The bias is small, on the order of 0.1 bpm. For T≥50 s, there are no invalid breathing rate estimates.

Breathing Detection

Operation of the breathing detection module 240 will now be explained. In one experimental embodiment, breathing detection is performed in a network-wide case using a normalized sum of the squared amplitudes $\hat{A}_l^2$ over all link l as given in equation (13). In one embodiment, $\hat{S}$ is calculated for each T second period for each RSS information 145 testing performance for each T in the range of 15 to 60 seconds, in 5 second intervals.

Figure 5:
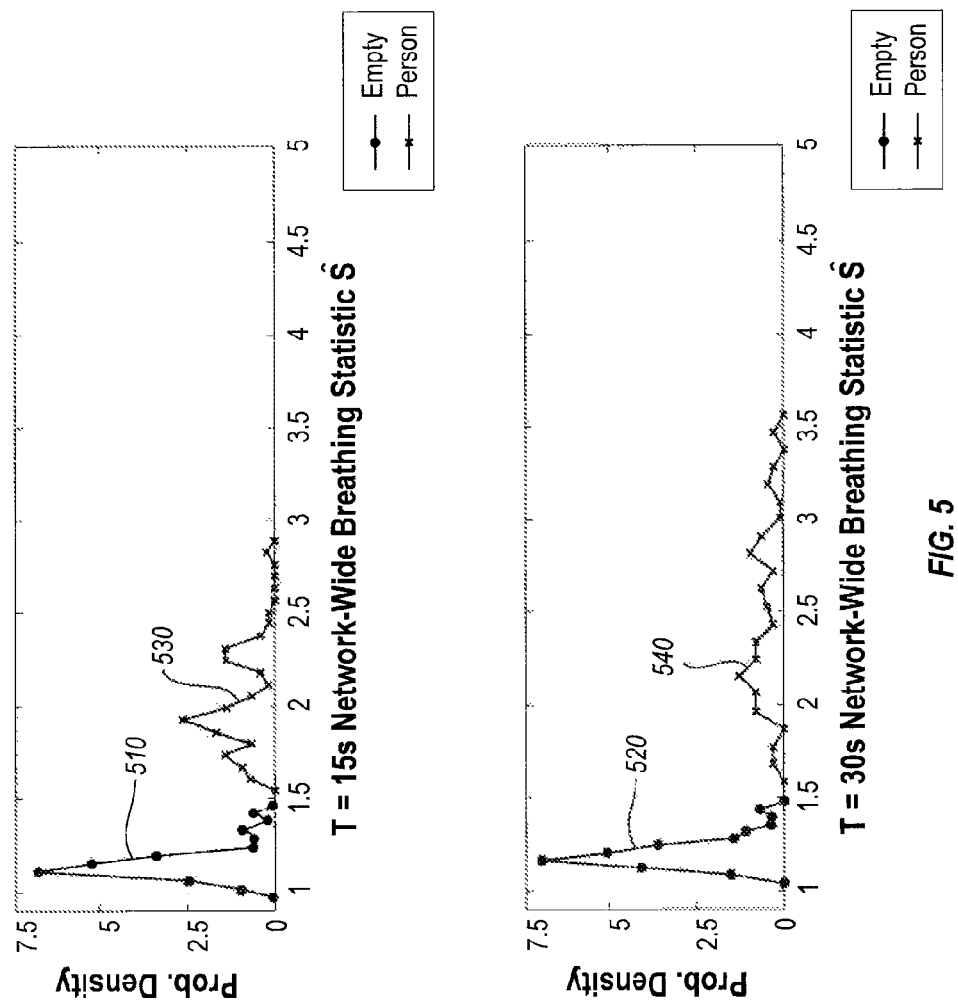
FIG. 5 illustrates probability density functions in accordance with an embodiment disclosed herein.

Turning to FIG. 5, probability density functions (pdfs) of $\hat{S}$ for $H_0$ and $H_1$ for T=15 (top subplot) and T=30 (bottom subplot) are shown. As can been seen the pdfs of $\hat{S}$ for $H_0$, denoted at 510 and 520, always fall in a narrow range between 0.98 and 1.45. In contrast, the pdfs of $\hat{S}$ for $H_1$, denoted at 530 and 540, have a value higher than 1.45, with a minimum in the T=15 being 1.57. Further, as T increases, the pdfs of $\hat{S}$ for $H_1$ also increase.

From this experimental embodiment, it can be concluded that the threshold 223 ($\gamma_{net}$) may be set to a value of 1.5 in equation (18). Thus, any time that the breathing detection module 240 uses equation (18) to determine the sum of the amplitudes of the RSS of each of the RSS information 145, an amplitude value below 1.5 will specify that the subject 110 is not breathing or is not present. An amplitude value above 1.5 will specify that the subject 110 is breathing. Of course it will be appreciated that threshold 223 ($\gamma_{net}$) 1.5 is only an example and is not be considered limiting. Any reasonable threshold 223 ($\gamma_{net}$) may be utilized as circumstances warrant.

In some embodiments, the breathing detection module 240 or some other module of the computing system 240 may include an alarm module 245. In operation, the alarm module may be configured to generate an audio or visual alarm anytime the breathing detection module 240 determines that the subject 110 is not breathing in the manner previously described. In other embodiments, the alarm module 245, for example, may provide wireless alerts (i.e. text messages, pages, or other alerts) to attending physicians or nurses.

Phase Estimation

As previously described, the computing system 160 may also include a phase estimation module 260. In some embodiments, the phase estimation module 260 may determine information about the subject 110's breathing by analyzing the phase of the sinusoidal signal. For example, if two sensor 130 links measure a sinusoid caused by the subject 110 breathing, both links should be synchronous, that is, rise or fall at the same times. However, typically it is not known whether inhaling will increase or decrease the RSS on any particular link, so one link may reach a maximum while another link reaches its minimum. In terms of phase, the $\{\hat{\phi}l\}l$ might be $\pi$ radians apart from each other.

Figure 6:
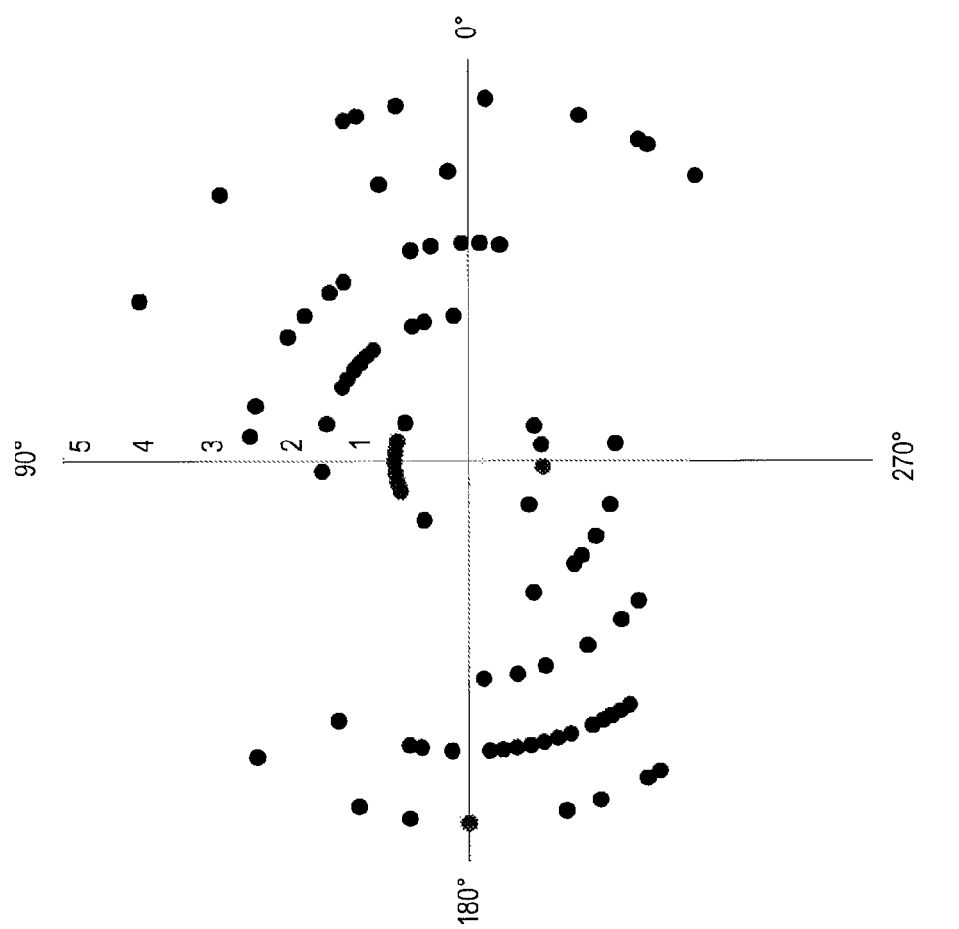
FIG. 6 illustrates phase measurements in accordance with an embodiment disclosed herein.

This is illustrated in FIG. 6, which shows the phase of five different experiments using the phase estimation module 260. As seen in FIG. 6, the five experiments are denoted as 1-5, each having its own concentric circle. Each experiment's $\hat{\phi}l$ values are plotted on a respective concentric circle. As can be seen, each experiment is seen to be bimodal, with the modes being 180° or $\pi$ radians apart.

Since the two links show the 180° relationship, in some embodiments the phase estimation module 260 may be able to make use of this fact to estimate the number of subjects 110 within a structure 120. This is best illustrated by reference to FIG. 7.

Figure 7:
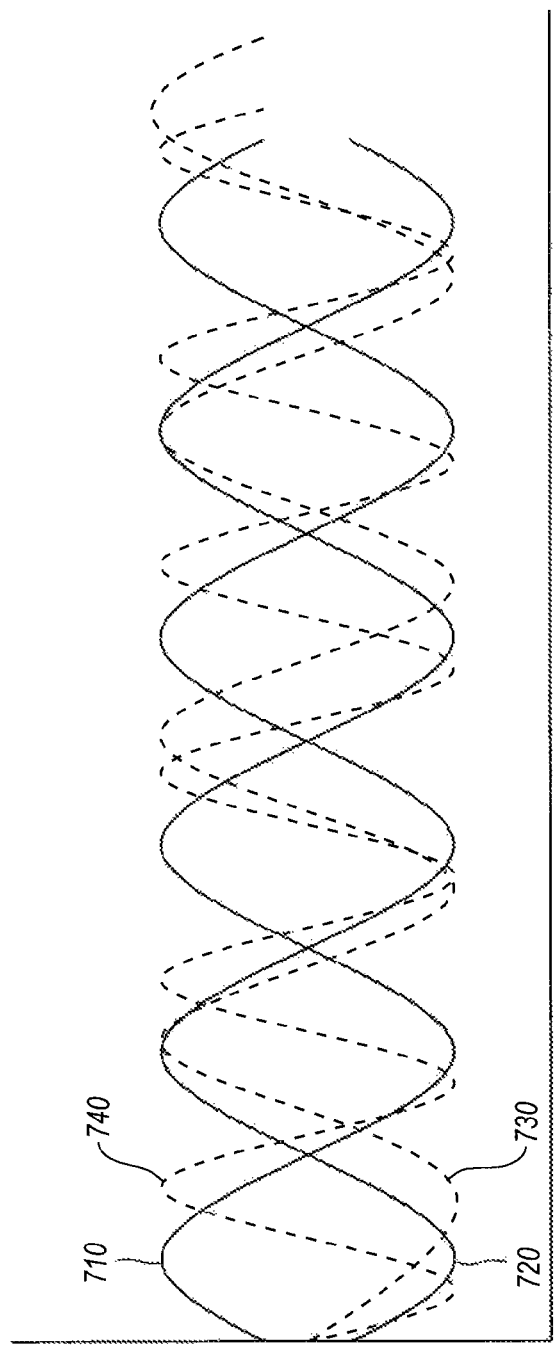
FIG. 7 illustrates shows a plot that shows amplitude versus phase in accordance with an embodiment disclosed herein.

FIG. 7 shows a plot 700 that shows amplitude versus phase of RSS information 145 measured by four links of sensor 130. A signal measured by a first link is illustrated at 710 and a signal measured by a second link is illustrated at 720. As expected, the two signals measured on these links are 180° apart from each other. It may be inferred that the breathing of a first subject 110 is being detected.

The plot 700 also shows a signal measured by a third link illustrated at 730. In addition, a signal measured by a forth link illustrated at 740 is 180° apart from the signal 730. The signals 730 and 740 are offset by some degrees from the signals 710 and 720. Since the signals 730 and 740 are offset from the signal 710 and 720, it may be inferred that the breathing of a second subject 110 is being detected since the breathing pattern of the second subject 110 will be different from the breathing pattern of the first subject 110. As will be appreciated, the phases of any number of additional links may be determined to detect the breathing of additional subjects 110.

Breathing Localization

Figure 8:
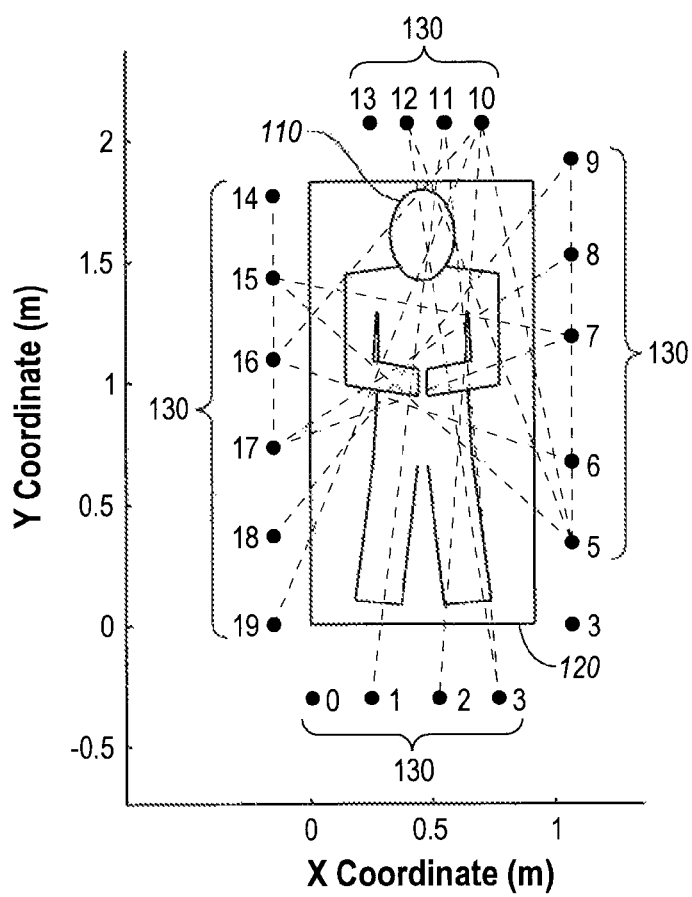
FIG. 8 illustrates high amplitude links in accordance with an embodiment disclosed herein.

Attention is now given to FIG. 8, which illustrates an embodiment similar to that of FIG. 1. FIG. 8 shows in dashed lines those high amplitude links that cross the subject 110, especially those that cross the chest of the subject 110. In some embodiments, the computing system 160 may use the information from these high amplitude links to determine the location of the subject 110 inside of the structure 120 such as a building. The high amplitude links may be used to generate a likelihood model that may be used to determine the location of the subject 110.

Figure 12:
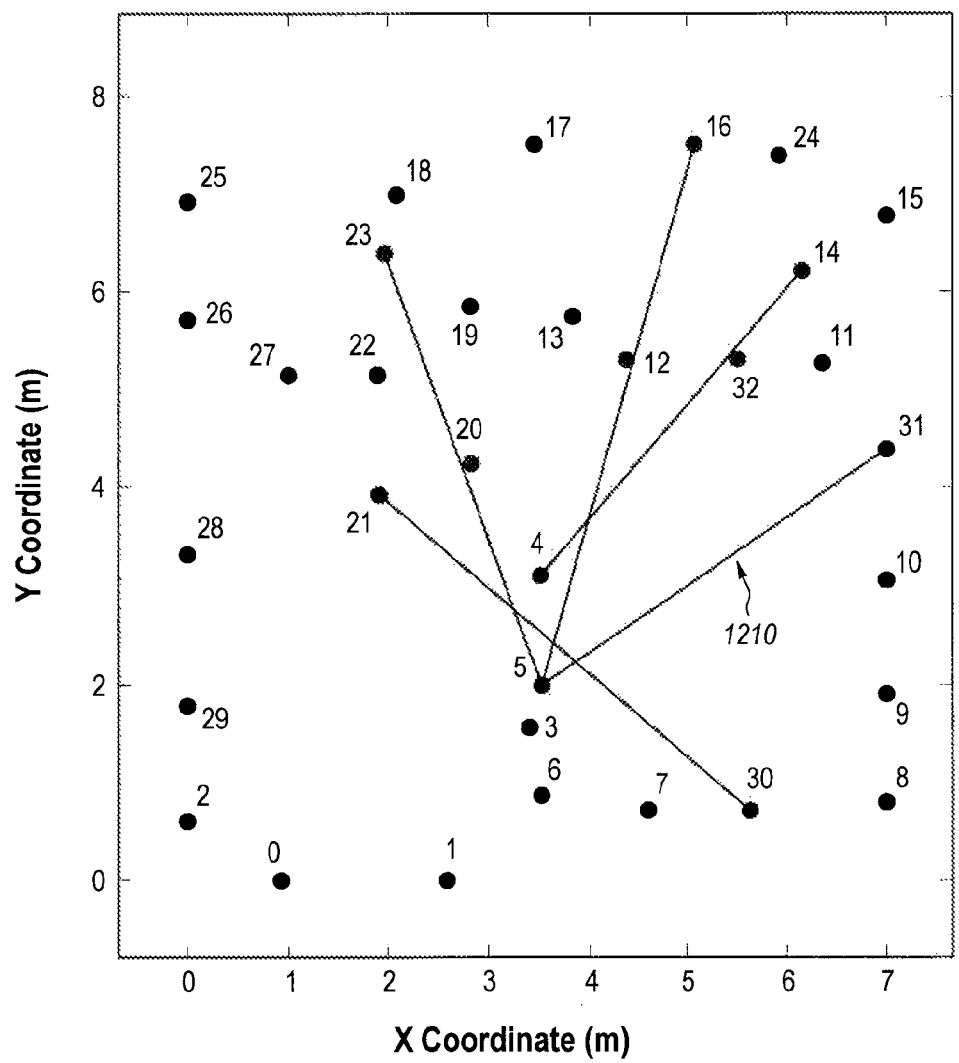
FIG. 12 illustrates high amplitude links when a subject is within the apartment of FIG. 9 in accordance with an embodiment disclosed herein.

FIG. 12 illustrates an embodiment when a subject 110 is within the building 120 illustrated in FIG. 9. FIG. 12 shows the sensors 130, numbered 0-32, in the same locations as in FIG. 9. In this embodiment, the subject 110 is located on the sofa near to sensor 5 (see FIG. 9). FIG. 12 further shows the high amplitude links 1210 that cross near to the subject 110 located on the sofa. This data may be used to estimate the location of the subject 110. In some embodiments, the data from the high amplitude links may be used in the breathing localization model previously described to estimate the coordinates of the subject 110.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical non-transitory storage media. Computer-readable media that carry computer-executable instructions are transmission media. Thus, by way of example, and not limitation, embodiments of the invention can comprise at least two distinctly different kinds of computer-readable media: physical non-transitory storage media and transmission media.

Physical non-transitory storage media includes RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to physical storage media (or vice versa). For example, computer-executable instructions or data structures received over a network or data link can be buffered in RAM within a network interface module (e.g., a "NIC"), and then eventually transferred to computer system RAM and/or to less volatile physical storage media at a computer system. Thus, it should be understood that physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method for breathing rate estimation comprising:
arranging a plurality of radio frequency sensors in a network around a subject within a structure;
measuring received signal strengths (RSS) between the plurality of radio frequency sensors, wherein the measured RSS is at least partially indicative of breathing of the subject;
determining a breathing rate estimation model based on information related to the measured signal strengths, wherein determining a breathing rate estimation model comprises:
calculating, with a computer processor, a power spectral density versus frequency of the measured RSS, and
identifying a frequency at which the power spectral density peaks,
wherein the identified frequency correlates with the estimated breathing rate of the subject; and
displaying an estimate of a breathing rate of the subject using the breathing rate estimation model.

2. The method of claim 1, wherein the breathing rate estimation model maximizes a function of the received signal strengths of a plurality of sensor pairs of the plurality of radio frequency sensors.

3. The method of claim 1, further comprising: estimating an amplitude of the signal strength at the estimated breathing rate using the breathing rate estimation model.

4. The method of claim 1, further comprising: estimating a phase of the signal strength at the estimated breathing rate using the breathing rate estimation model.

5. The method of claim 4, wherein the estimated phase of the signal strength is used to estimate the number of subjects within the structure.

6. The method of claim 1, wherein the plurality of radio frequency sensors do not touch the subject within the structure.

7. The method of claim 1, wherein the structure is a bed that the subject lies in.

8. The method of claim 1, wherein the structure is a building within which the subject is located.

9. The method of claim 8, wherein the plurality of radio frequency sensors are located within one or more walls of the building.

10. The method of claim 8, wherein the plurality of radio frequency sensors are attached to one or more walls of the building.

11. The method of claim 1, wherein the plurality of radio frequency sensors comprise multiple frequency channel sensors.

12. The method of claim 1, further comprising:
   determining a mean RSS value for the measured RSS;
   removing the mean RSS value from the measured RSS; and
   using the resultant RSS value in the breathing rate estimation model to determine the breathing rate of the subject.

13. The method of claim 12, wherein a filter is used to remove the mean RSS value.

14. The method of claim 12, wherein one or more time indices during which a RSS change occurs are used when removing the mean RSS value.

15. The method of claim 1, further comprising: using the estimated breathing rate to estimate a location of the subject within the structure.

16. A method for breathing detection comprising:
   arranging a plurality of radio frequency sensors in a network around a subject within a structure;
   measuring received signal strengths (RSS) between the plurality of radio frequency sensors, the received signals strengths is at least partially indicative of breathing of the subject;
   calculating a probability density function of a network-wide breathing statistic over all links of the plurality of radio frequency sensors for a given time unit, wherein the network-wide breathing statistic is calculated by a summing of RSS amplitudes over links in the network;
   comparing the probability density function to a user defined breathing threshold; and
   during time periods when the probability density function is below the threshold value indicating, on a digital display, that the subject is not breathing, and
   during time periods when the sum of the probability density function is above the threshold value indicating, on the digital display, that the subject is breathing.

17. The method according to claim 16, wherein the network-wide breathing statistic includes a determination of a normalized sum of the squared amplitudes of the signal strengths for all links of the plurality of radio frequency sensors and the user defined breathing threshold.

18. The method according to claim 17, wherein determining whether the subject is breathing or not comprises: comparing whether the normalized sum of the squared amplitudes is greater or less than the user defined breathing threshold, wherein when the amplitude is greater the subject is likely to be breathing and when the amplitude is less than the subject is likely not breathing.

19. The method of claim 16, wherein the plurality of radio frequency sensors do not touch the subject within the structure.

20. The method of claim 16, wherein the structure is a bed that the subject lies in.

21. The method of claim 16, wherein the structure is a building within which the subject is located.

22. The method of claim 21, wherein the plurality of radio frequency sensors are located within one or more walls of the building.

23. The method of claim 21, wherein the plurality of radio frequency sensors are attached to one or more walls of the building.

24. The method of claim 16, wherein the plurality of radio frequency sensors comprise multiple frequency channel sensors.

25. A method for estimating the location of a breathing subject within a structure comprising:
   obtaining a breathing rate estimate of a subject within a structure, the breathing rate estimate based at least in part on a measured signal strength obtained from a plurality of radio frequency sensors placed within the structure;
   identifying, with a breathing localization model, high amplitude links between one or more of the plurality of radio frequency sensors that generated higher amplitudes of signal strength than the other radio frequency sensors;
   identifying the link distance between the receiving portion and transmitting portion of each high amplitude link;
   mapping the detected high amplitude links and respective link distances to a pixel map representative of the structure;
   estimating the location of the subject within the structure based on the coordinates obtained from the pixel map; and
   displaying, on a digital display, an estimated location of the subject within the structure.

26. The method of claim 25, wherein the structure is a building within which the subject is located.

27. The method of claim 26, wherein the plurality of radio frequency sensors are located within one or more walls of the building.

28. The method of claim 26, wherein the plurality of radio frequency sensors are attached to one or more walls of the building.

29. The method of claim 25, wherein the plurality of radio frequency sensors comprise multiple frequency channel sensors.

30. A system for breathing estimation comprising:
   a plurality of radio frequency sensors associated with a structure within which a breathing subject is located; and
   a computing system including a breathing rate estimation module, the breathing rate estimation module configured to obtain information related to received signal strengths between the plurality of radio frequency sensors and to perform the following:
      calculate, with a computer processor, a power spectral density versus frequency of the measured RSS; and
      identify a frequency at which the power spectral density peaks,
      wherein the identified frequency correlates with the estimated breathing rate of the subject;
      determine a breathing rate estimation model based on the measured signal strengths, wherein determining a breathing rate estimation model comprises:
         calculating, with a computer processor, a power spectral density versus frequency of the measured RSS, and
         identifying a frequency at which the power spectral density peaks,
         wherein the identified frequency correlates with the estimated breathing rate of the subject; and
      displaying an estimate of a breathing rate of the subject using the breathing rate estimation model.

31. The system of claim 30, further comprising: a base station sensor for collecting the information related to the received signal strengths between the plurality of radio frequency sensors, the base station sensor providing the information to the computing system.

32. The system of claim 30, wherein the plurality of radio frequency sensors comprise multiple frequency channel sensors.

33. The system of claim 30, wherein the breathing rate estimation module is further configured to perform the following:
   determine a mean RSS value for the measured RSS;
   remove the mean RSS value from the measured RSS; and
   use the resultant RSS value in the breathing rate estimation model to determine the breathing rate of the subject.

34. The system of claim 33, further comprising a filter that is used to remove the mean RSS value.

35. The system of claim 33, the breathing rate estimation module uses one or more time indices during which a RSS change occurs when removing the mean RSS value.

36. The system of claim 30, the breathing rate estimation module uses the estimated breathing rate to estimate a location of the subject within the structure.

37. The system of claim 30, wherein the structure is a bed that the subject lies in.

38. The system of claim 30, wherein the structure is a building within which the subject is located.

39. The system of claim 38, wherein the plurality of radio frequency sensors are located within one or more walls of the building.

40. The system of claim 38, wherein the plurality of radio frequency sensors are attached to one or more walls of the building.

41. A system for breathing detection comprising:
   a plurality of radio frequency sensors associated with a structure within which a breathing subject is located; and
   a computing system including a breathing detection module, the breathing detection module configured to obtain information related to received signal strengths of the plurality of radio frequency sensors and to perform the following:
      calculate a network-wide breathing statistic over all links of the plurality of radio frequency sensors, wherein the network-wide statistic is calculated by a summing of RSS amplitudes over links in the network;
      comparing the sum of the RSS amplitudes to a user defined breathing threshold value; and
      when the sum of the RSS amplitudes is below the threshold value displaying on a digital display an indication that the subject is not breathing, and
      when the sum of the RSS amplitudes is above the threshold value displaying on the digital display an indication that the subject is breathing.

42. The system of claim 41, further comprising: a base station sensor for collecting the information related to the received signal strengths between the plurality of radio frequency sensors, the base station sensor providing the information to the computing system.

43. The system of claim 41, wherein the plurality of radio frequency sensors comprise multiple frequency channel sensors.

44. The system of claim 41, wherein the structure is a bed that the subject lies in.

45. The system of claim 41, wherein the structure is a building within which the subject is located.

46. The system of claim 45, wherein the plurality of radio frequency sensors are located within one or more walls of the building.

47. The system of claim 45, wherein the plurality of radio frequency sensors are attached to one or more walls of the building.

48. A system for estimating the location of a breathing subject within a structure comprising:
   a plurality of radio frequency sensors associated with a structure within which a breathing subject is located; and
   a computing system including a breathing localization module, the breathing localization module configured to obtain information related to received signal strengths of the plurality of radio frequency sensors and to perform the following:
      obtain a breathing rate estimate of a subject within the structure, the breathing rate estimate based at least in part on the received signal strengths obtained from the plurality of radio frequency sensors placed within the structure;
      identifying high amplitude links between one or more of the plurality of radio frequency sensors that generated higher amplitudes of signal strength than the other radio frequency sensors;
      identifying the link distance between the receiving portion and transmitting portion of each high amplitude link;
      mapping the identified high amplitude links and respective link distances to a pixel map representative of the structure; and
      estimate the location of the subject within the structure based on the coordinates obtained from the pixel map; and
      displaying, on a digital display, an estimated location of the subject within the structure.

49. The system of claim 48, wherein the plurality of radio frequency sensors comprise multiple frequency channel sensors.

50. The system of claim 48, wherein the structure is a building within which the subject is located.

51. The system of claim 50, wherein the plurality of radio frequency sensors are located within one or more walls of the building.

52. The system of claim 50, wherein the plurality of radio frequency sensors are attached to one or more walls of the building.

53. The system of claim 48, wherein an image vector is used when estimating the coordinates.

* * * * *